United States Patent [19]

Schaar

[11] 4,341,209
[45] Jul. 27, 1982

[54] ADHESIVE BANDAGE WITH FOAM BACKING

[75] Inventor: Charles H. Schaar, Lake Zurich, Ill.

[73] Assignee: The Kendall Company, Walpole, Mass.

[21] Appl. No.: 224,378

[22] Filed: Jan. 12, 1981

[51] Int. Cl.³ .............................................. A61L 15/00
[52] U.S. Cl. ..................................... 128/156; 428/343
[58] Field of Search .............................. 128/155–156; 428/261, 343

[56] References Cited

U.S. PATENT DOCUMENTS

| | | | |
|---|---|---|---|
| 3,487,832 | 1/1970 | Spence | 128/156 |
| 3,525,340 | 8/1970 | Gilbert | 128/155 |
| 3,973,563 | 8/1976 | Green et al. | 128/156 |
| 4,251,584 | 2/1981 | vanEngelen et al. | 428/343 |

Primary Examiner—C. Fred Rosenbaum

[57] ABSTRACT

The pressure sensitive adhesive bandage disclosed includes a novel low density polyethylene closed cell foam backing sheet with a glossy, smoothly pebbled, low friction, non-adherent face surface and a coating-adherent rear surface having a pressure sensitive adhesive to which is adhered an absorbent pad. In comparison with bandages having a vinyl backing sheet, the novel plasticizer-free polyethylene foam backing sheet provides improved shelf life, while its low density and low hand provides superior smoothness, flexibility, conformability and softness.

4 Claims, 4 Drawing Figures

ADHESIVE BANDAGE WITH FOAM BACKING

This invention relates to pressure sensitive adhesive bandages and, more particularly, to novel backing sheets for such bandages.

Pressure sensitive adhesive bandages, such as finger bandages and the like, including a backing sheet having thereon a coating of pressure sensitive adhesive and an absorbent pad, are in wide use. The backing sheet of such bandages is commonly of solid vinyl sheet material, usually of about 3 mil thickness. Although such vinyl sheet material is entirely satisfactory in regard to its tensile strength and elasticity, it is somewhat deficient in regard to its smoothness, flexibility, conformability and softness, particularly when used as a finger bandage. Furthermore, since vinyl contains plasticizers, when the adhesive is applied to the vinyl sheet backing material during the manufacture of such bandages, the plasticizers begin to migrate into the adhesive, with the result that the adhesive gradually loses its adhesion and so limits the shelf life of the bandages.

In view of the above deficiencies of the prior art vinyl sheet backing material it is a major object of my present invention to provide a pressure sensitive adhesive bandage having superior smoothness, flexibility, conformability and softness, as well as one which has a greatly increased shelf life.

In my studies, I have discovered, unexpectedly, that the smoothness, flexibility, conformability and softness of such bandages is to a substantial degree determined by the density and hand of the backing sheet material, "hand" being a combined measurement of the surface friction and flexural rigidity of the backing sheet material, as measured by standard test procedures hereinafter more fully explained. In view of such studies, I have concluded that a bandage having smoothness, flexibility, conformability and softness superior to that provided by the conventional vinyl backing sheet could be achieved by utilizing a sheet material of equivalent thickness, having adequate strength and elasticity, but having values of both density and hand substantially lower that those of vinyl sheet material.

In accordance with the above conclusion, I have provided a novel pressure sensitive adhesive bandage having superior smoothness, flexibility, conformability and softness, including a backing sheet with a coating of pressure sensitive adhesive providing an adhesive rear surface, and an absorbent pad adhered to a portion of its adhesive rear surface with other portions of the adhesive rear surface being left uncovered.

By my invention, I have provided a novel adhesive bandage by utilizing a backing sheet of polyethylene foam film with predominently closed cells, of between about 2 to 7 and preferably about 3 to 4 mils thickness, and with a glossy, smoothly pebbled, low friction, non-adherent face surface and a coating-adherent rear surface having adhered thereon a coating of pressure sensitive adhesive to provide the adhesive rear surface. In accordance with my invention, the polyethylene foam film thereof has an apparent effective density of less than about 1.00 grams per cubic centimeter, preferably less than about 0.60 grams per cubic centimeter and a TAPPI T498 hand of less than about 25 grams and preferably less than about 15 grams. In contrast, the density and hand values of the novel polyethylene closed cell foam sheet backing material of the bandage of my invention are far lower than those of typical examples of the conventional 3 mil solid vinyl sheet backing material, of which the density is typically about 1.25 grams per cubic centimeter, and the hand between about 30 to 50 grams.

In comparison, the density of a typical example of the novel polyethylene closed cell 3 mil thick foam sheet material utilized in the bandage of my invention is about 0.55 grams per cubic centimeter and the hand is less than about 15 grams, much less than that of a vinyl backing sheet of equivalent thickness. These substantially lower values of density and hand provide a bandage having smoothness, flexibility, conformability and softness far superior to that of one utilizing solid vinyl sheet material of equivalent thickness, while at the same time providing a backing of adequate strength and elasticity.

Furthermore, since the novel polyethylene foam sheet backing material of the bandage of my invention does not contain plasticizers, it has a greatly extended shelf life compared to bandages having vinyl backing sheet material.

For the purpose of explaining still further objects and features of my invention, reference is now made to the following detailed description of a preferred embodiment thereof, together with the accompanying drawings, wherein.

Figure 1:
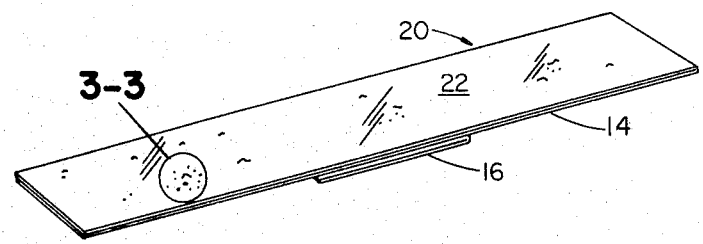
FIG. 1 is an isometric view of the face of the novel bandage of my invention.
Figure 2:
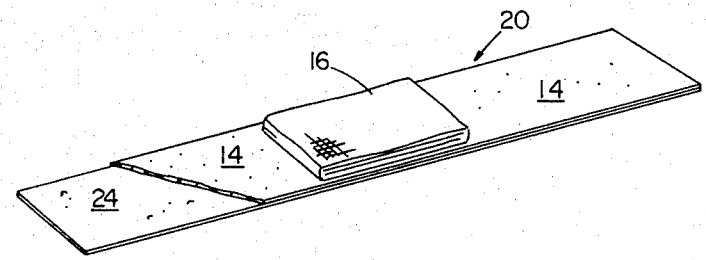
FIG. 2 is an isometric view of the rear of the bandage of FIG. 1.

Referring to the drawings, the pressure sensitive adhesive bandage of the present invention has a novel backing sheet, generally designated 20, which has a glossy, smoothly pebbled, low friction, non-adherent face surface 22 and a rear surface 24 which has been treated by corona discharge to provide a coating-adherent surface to which a pressure sensitive adhesive coating 14 is adhered to provide an adhesive rear surface. Any of a variety of well-known pressure sensitive adhesives may be used to provide a coating 14 of between about 0.50 to 2.0 mils thick, with 1.0 to 1.5 mils being preferred. A conventional absorbent pad 16 is adhered to the central portion of pressure sensitive adhesive rear surface coating 14 with other portions of adhesive rear surface coating 14 remaining uncovered for securing the bandage in use.

Figure 3:
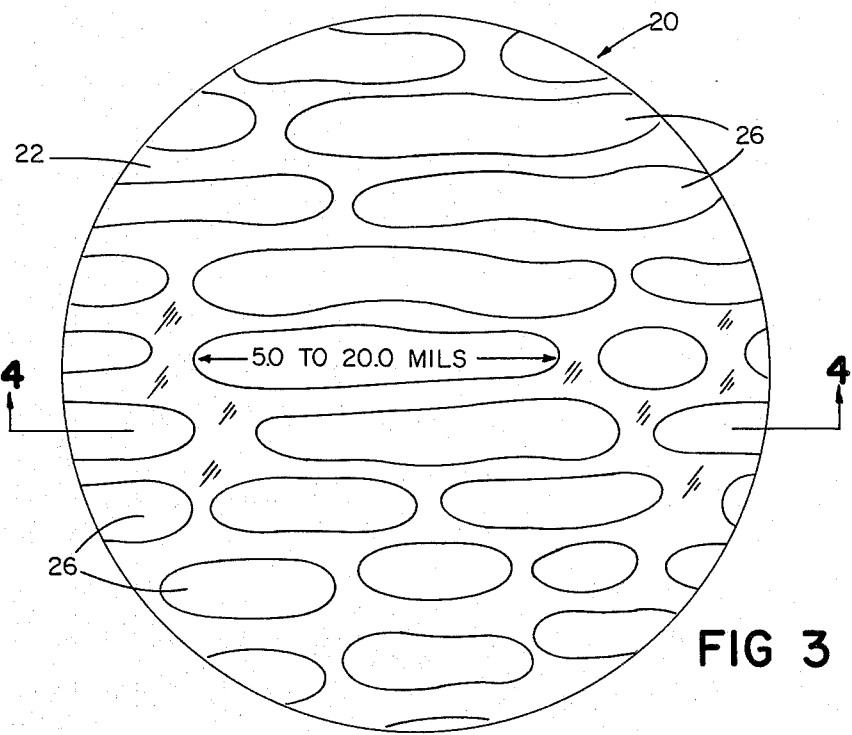
FIG. 3 is an enlarged view of the face of the bandage of FIG. 1, taken within line 3—3 of FIG. 1.
Figure 4:
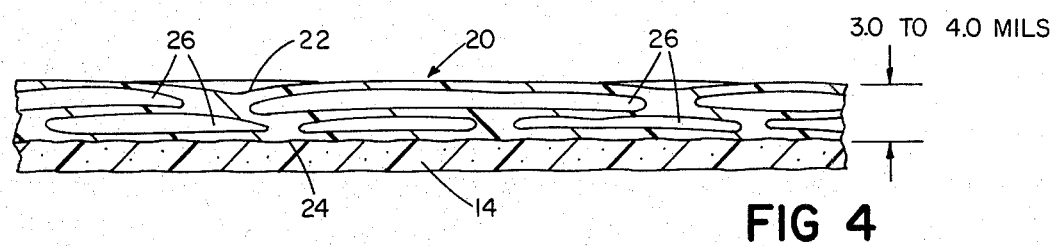
FIG. 4 is a cross section view of the bandage of FIG. 1, taken along line 4—4 of FIG. 3.

More specifically, as best shown in FIGS. 3 and 4, backing sheet 20 preferably comprises a polyethylene foam film marketed by Deerfield Plastics Co., Inc. of South Deerfield, Mass., identified as PE #3 White Sheeting, which has a thickness between 3.0 to 4.0 mils with closed cells 26 of generally lenticular shape therein which have major axes of between 5.0 to 20.0 mils and thickness dimensions of substantially less than the film thickness. Backing sheet 20 has an effective density of less than 0.60 grams per cubic centimeter and an TAPPI T498 hand of less than 15 grams.

Hand is a combined measurement of the surface friction and flexural rigidity of sheet material, as measured by standard test procedures on a Handle-O-Meter, manufactured by Thwing-Albert Instrument Company of Philadelphia, Pa. The test procedure used may be either the INDA (International Nonwoven and Disposable Associates) 90.0-75 (R77) or the TAPPI (Technical Association of Pulp and Paper Industry) T498, conducted at a relative humidity of 54 percent and a temperature of 76 degrees F.

In the TAPPI T498 hand test, the machine measures the resistance of a test material to the movement of a machine arm as it moves the test material through a slot, the resulting measurement being given in grams. The machine slot has a width of ⅝ inches. The hand is an average of the measurements at various positions on the test material, with a lesser resistance indicating a softer material.

Specific embodiments of the novel adhesive bandage backings, in accordance with the present invention are illustrated by the following representative examples. It will be understood, however, that the invention is not confined to the specific limitations set forth in the individual examples, but rather to the scope of the appended claims.

EXAMPLE 1

|  | Foam | Vinyl* |
|---|---|---|
| Area | 3¼" × 3¼" | 3¼" × 3¼" |
| Thickness | 3.7 mils | 3.1 mils |
| Hand** | 23.0 grams | 40.8 grams |

EXAMPLE 2

|  | Foam | Vinyl* |
|---|---|---|
| Area | 4" × 4" | 4" × 4" |
| Thickness | 3.0 mils | 3.0 mils |
| Hand** | 13.0 grams | 47.1 grams |

EXAMPLE 3

|  | Foam | Vinyl* |
|---|---|---|
| Area | 3¼" × 3¼" | 3¼" × 3¼" |
| Thickness | 3.5 mils | 3.0 mils |
| Hand** | 22.1 grams | 32.1 grams |

*Goodyear Clear Film P90-8156
**TAPPI T498

As shown in EXAMPLES 1 and 3, if the thickness of foam film backing sheet 20 and the conventional vinyl backing sheet had been the same, the hand for foam film backing sheet 20 would have been even smaller.

Various modifications of the herein described pressure sensitive adhesive bandages, within the spirit and scope of the appended claims, will be apparent to those skilled in the art.

What is claimed is:

1. A pressure sensitive adhesive bandage having superior smoothness, flexibility, conformability and softness, including
   a backing sheet with a glossy, smoothly pebbled, low friction, non-adherent face surface and a coating-adherent rear surface having adhered thereon a coating of pressure sensitive adhesive providing an adhesive rear surface, and
   an absorbent pad adhered to a portion of said adhesive rear surface with other portions of said adhesive rear surface being uncovered
   said backing sheet comprising
   polyethylene foam film of between about 2 to 7 mils thickness with predominently closed cells, an apparent effective density of less than about 1.00 gram per cubic centimeter, and a TAPPI T498 hand of less than a vinyl backing sheet of equivalent thickness.

2. A pressure sensitive adhesive bandage having superior smoothness, flexibility, conformability and softness, including
   a backing sheet with a glossy, smoothly pebbled, low friction, non-adherent face surface and a coating-adherent rear surface having adhered thereon a coating of pressure sensitive adhesive providing an adhesive rear surface, and
   an absorbent pad adhered to a portion of said adhesive rear surface with other portions of said adhesive rear surface being uncovered
   said backing sheet comprising
   polyethylene foam film of between about 2 to 7 mils thickness with predominently closed cells, an apparent effective density of less than about 0.75 grams per cubic centimeter and a TAPPI T498 hand of less than about 25 grams.

3. A pressure sensitive adhesive bandage having superior smoothness, flexibility, conformability and softness, including
   a backing sheet with a glossy, smoothly pebbled, low friction, non-adherent face surface and a coating-adherent rear surface having adhered thereon a coating of pressure sensitive adhesive providing an adhesive rear surface, and
   an absorbent pad adhered to a portion of said adhesive rear surface with other portions of said adhesive rear surface being uncovered
   said backing sheet comprising
   polyethylene foam film of between about 3 to 4 mils thickness with predominently closed cells, an apparent effective density of less than about 0.60 grams per cubic centimeter and a TAPPI T498 hand of less than about 15 grams.

4. The pressure sensitive adhesive bandage as claimed in claim 1, 2 or 3, wherein
   said film has closed cells having maximum dimensions in the plane of said sheet of from about 5 to 20 mils.

* * * * *